United States Patent [19]

November

[11] 4,023,400
[45] May 17, 1977

[54] VISCOSIMETER AND/OR DENSITOMETER

[75] Inventor: Milton H. November, Hacienda Heights, Calif.

[73] Assignee: International Telephone and Telegraph Corporation, New York, N.Y.

[22] Filed: Aug. 23, 1976

[21] Appl. No.: 716,823

[52] U.S. Cl. ............................................. 73/54
[51] Int. Cl.² ....................................... G01N 11/16
[58] Field of Search .................. 73/32 A, 54, 59

[56] References Cited

UNITED STATES PATENTS

| | | |
|---|---|---|
| 3,382,706 | 5/1968 | Fitzgerald et al. ................. 73/54 X |
| 3,712,117 | 1/1973 | Fitzgerald et al. ..................... 73/59 |
| 3,832,884 | 9/1974 | Schlatter ........................... 73/32 A |
| 3,878,374 | 4/1975 | Schlatter ...................... 73/32 A X |
| 3,903,732 | 9/1975 | Rork et al. ............................ 73/54 |
| 3,943,753 | 3/1976 | Simon .................................. 73/54 |

*Primary Examiner*—Richard C. Queisser
*Assistant Examiner*—Joseph W. Roskos
*Attorney, Agent, or Firm*—A. Donald Stolzy

[57] ABSTRACT

An electromechanical oscillator having a feedback shifted alternately to two different phases, and two digital function generators to derive viscosity and density signals on a time shared basis.

7 Claims, 7 Drawing Figures

VISCOSIMETER AND/OR DENSITOMETER

BACKGROUND OF THE INVENTION

This invention relates to the art of examining a fluid property, and more particularly to viscosimeters and/or vibration densitometers.

SUMMARY OF THE INVENTION

In accordance with the present invention, the complex character of the prior art is overcome by providing a feedback of a certain phase.

The above-described and other advantages of the present invention will be better understood from the following detailed description when considered in connection with the accompanying drawings.

BRIEF DESCRIPTION OF THE DRAWINGS

In the drawings, which are to be regarded as merely illustrative.

DESCRIPTION OF THE PREFERRED EMBODIMENTS

Figures 1, 4:
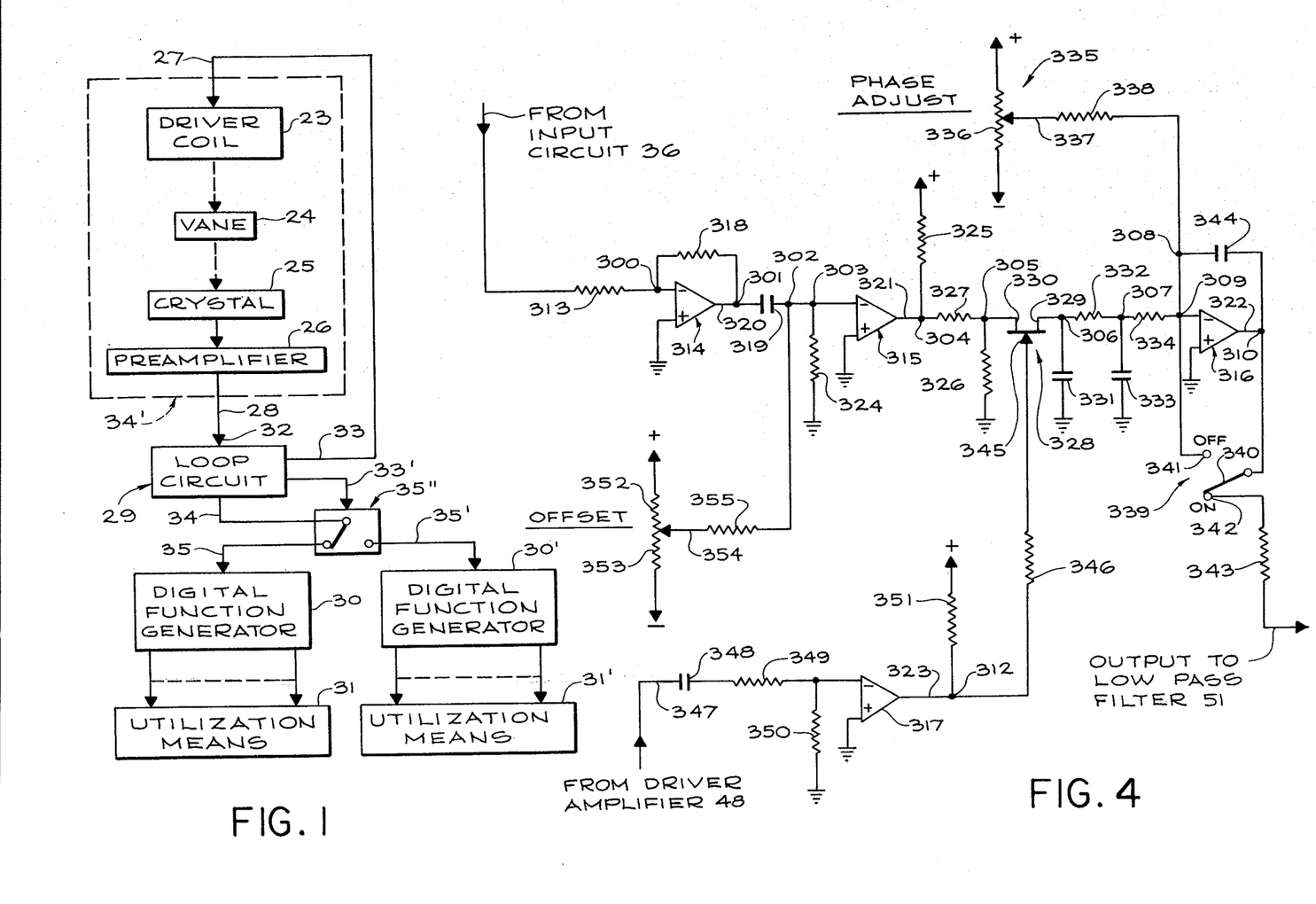
FIG. 1 is a block diagram of a densitometer constructed in accordance with the present invention.
FIG. 4 is a schematic diagram of a phase detector shown in FIG. 2.

In the drawings, in FIG. 1, a vibration viscosity of densitometer probe is indicated at 34' having a driver coil 23, a vane 24, a piezoelectric crystal 25 and a preamplifier 26.

Probe 34' has an input lead 27 and an output lead 28.

Other blocks shown in FIG. 1 are a loop circuit 29, digital function generators 30 and 30' and utilization means 31 and 31'. Loop circuit 29 has an input lead 32 and output leads 33, 33' and 34. Digital function generators 30 and 30' have input leads 35 and 35' connected from loop circuit 29 via lead 34 and an electronic switch 35''. The outputs of digital function generators 30 and 30' are connected to utilization means 31 and 31'.

The output lead 28 of probe 34' is connected to the input lead 32 of loop circuit 29. The input lead 27 of probe 34' is connected from the output lead 33 of loop circuit 29. Probe 34' and loop circuit 29 form a closed loop electromechanical oscillator. Vane 24 is submerged in a fluid. The viscosity or density of the fluid is a function of the frequency at which vane 24 vibrates.

Digital function generator 30 may have its input lead 35 connected from lead 34 or at other points in loop circuit 29. Loop circuit 29 impresses a square wave voltage on one of the input leads 35 and 35' of digital function generators 30 and 30', respectively. The square wave may have a mark-to-space ration of 1:1.

Utilization means 31 and 31' shown in FIG. 1 may be density and viscosity indicators, respectively, specific gravity and viscosity indicators, respectively, and one or more process controllers or otherwise.

Probe 34', digital function generator 30 and utilization means 31 may be identical to those disclosed in U.S. Pat. No. 3,878,374. The same is true of everything shown in FIGS. 2 and 3, but not phase detector 50' or dividers 400, 401 and 402 shown in FIG. 2.

Probe 34' shown in FIG. 1 may be conventional.

Preamplifier 26 shown in FIG. 1 may be conventional. Preamplifier 26 may also be conventional.

Figure 2:
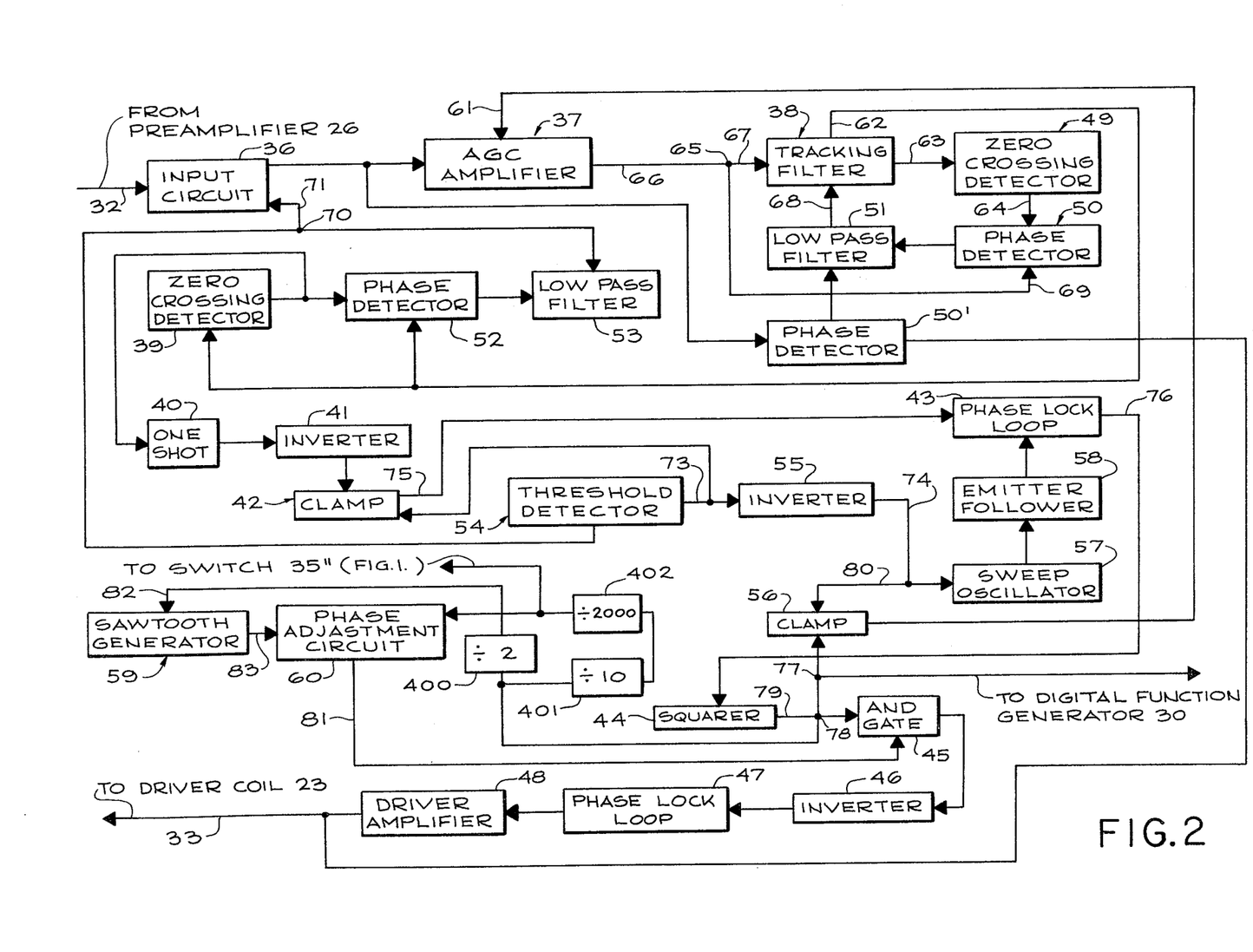
FIG. 2 is a block diagram of a loop circuit shown in FIG. 1.

Loop circuit 29 is shown in FIG. 2 including an input circuit 36, an AGC amplifier 37, a tracking filter 38, a zero crossing detector 39, a one-shot multivibrator 40, an inverter 41, a clamp 42, a phase lock loop 43, a squarer 44, an AND gate 45, an inverter 46, a phase lock loop 47 and a driver amplifier 48 connected in succession as serial stages from input lead 32 of loop circuit 29 to its output lead 33 is connected respectively from the output lead 28 of probe 34' and to the input lead 27 of probe 34'.

In FIG. 2, other stages are a zero crossing detector 49, a phase detector 50, a low pass filter 51, a phase detector 52, a low pass filter 53, a threshold detector 54, an inverter 55, a clamp 56, a sweep oscillator 57, an emitter-follower 58, a saw-tooth generator 59 and a phase adjustment circuit 60 (manually adjustable only).

AGC amplifier 37 has an AGC input lead 61 connected from the output of clamp 56.

Tracking filter 38 has two output leads 62 and 63. Tracking filter output lead 63 is connected to the input of zero crossing detector 49. The output of zero crossing detector 49 is connected to one input 64 of phase detector 50. A junction is provided at 65 from which an output lead 66 of AGC amplifier 37 is connected. Tracking filter 38 has two input leads 67 and 68. Tracking filter input lead 67 is connected from junction 65. Lead 68 is connected from the output of low pass filter 51.

Phase detector 50 has a second input lead 69 connected from junction 65. The output of phase detector 50 is connected to one input of low pass filter 51. Phase detector 50' has one input connected from the output of input circuit 36 and another input connected from lead 33. Phase detector 50' has an output connected to another input of low pass filter 51.

The purpose of zero crossing detector 49, phase detector 50 and low pass filter 51 is to cause tracking filter 38 to track the frequency of output signal of AGC amplifier 37. Phase detector 50' causes the output of driver amplifier 48 to track the phase (have a constant phase difference relative to that) of the output signal of input circuit 36. The signal on the tracking filter 38, thus, causes the passband thereof to straddle the frequency of the input to tracking filter 38 over input lead 67, and to track the phase thereof as well.

The output of tracking filter 38 on output lead 62 thereof is 90 degrees out of phase with the signal on the output lead 63 thereof. The signal from the tracking filter output lead 62 is impressed upon zero crossing detector 39 and phase detector 52. The output of zero crossing detector 39 is impressed both upon phase detector 52 and one-shot 40. The output of phase detector 52 is impressed upon low pass filter 53.

A junction is provided at 70 connected from the output of low pass filter 53. A lead 71 is connected from junction 70 to input circuit 36 to the AGC input of an amplifier therein for automatic gain control.

Threshold detector 54 has an input connected from junction 70. This input of threshold detector 54, when below a predetermined potential, causes the potential of the output lead 73 of threshold detector 54 to go either high or low. The output lead 73 of threshold detector 54 is, thus, for example, either ground or +15 volts or +V1. When the output of low pass filter 53 is below the predetermined potential, output lead 73 of threshold detector 54 is at ground.

Threshold detector 54 operates both of the clamps 42 and 56 and the sweep oscillator 57. Clamp 56 and sweep oscillator 57 are operated through the inverter 55.

Inverter 55 has an output lead 74 which also assumes potentials of V1 or ground.

Clamp 42 either passes the output of inverter 41 to the phase lock loop 43 of in the other state of the threshold detector 54, clamp 42 having an output lead 75, is operated to clamp the output lead 75 to ground. The output of inverter 55 is simply the inverse of the output of threshold detector 54. When the output of inverter 55 is high, sweep oscillator 57 receives power. When the output of inverter 55 is low, the output of sweep oscillator 57 is at ground.

Emitter follower 58 is connected between sweep oscillator 57 and phase lock loop 43. Phase lock loop 43 has an output lead 76 which is connected to squarer 44. Junctions are provided at 77 and 78. Squarer 44 has an output lead 79 connected to junction 78. Junction 78 is connected to junction 77. Clamp 56 is connected from junction 77 to AGC amplifier input lead 61.

When the output of threshold detector 54 is high, loop circuit 29 is tracking and opens clamp 42 to unground the output lead 75 thereof. Conversely, at the same time, inverter 55 grounds the input to sweep oscillator 57 and disables it. During tracking, inverter 55 also disables the output of clamp 56 by a connection 80 from inverter output lead 74 to clamp 56.

During searching, threshold detector 54 holds the output of clamp 42 at ground while inverter 55 operates sweep oscillator 57 and clamp 56 passes the output of squarer 44 to the AGC input lead 61 of AGC amplifier 37.

In FIG. 2, junction 77 is connected to switch 35" shown in FIG. 1.

AND gate 45 receives an input from junction 78 and from an output lead 81 of phase adjustment circuit 60.

Sawtooth generator 59 has an input lead 82 connected from junction 78 through divider 400, and an output lead 83 connected to an input of phase adjustment circuit 60.

Circuit 60 is manually adjustable to manually adjust the sine wave component of the output voltage of driver amplifier 48 through the use of certain structures including the phase adjustment circuit 60 itself, and phase lock loop 47. This adjustment can make the electromechanical oscillator oscillate with maximum efficiency.

OPERATION

In the embodiment of the invention shown in FIG. 1, probe 34' and loop circuit 29 provide an electromechanical oscillator which oscillates at a frequency dependent upon the viscosity or density of the fluid in which vane 24 is immersed. The same is true of the pulse repetition frequency of the square wave voltage applied to the input leads 35' and 35, respectively, of digital function generators 30 and 30'.

Digital function generators 30 and 30' may be described as digital linearization circuits. Each produces a digital output directly proportional to density and viscosity, respectively, from the input signal thereto impressed upon the respective input leads 35 and 35' thereto.

Figure 3:
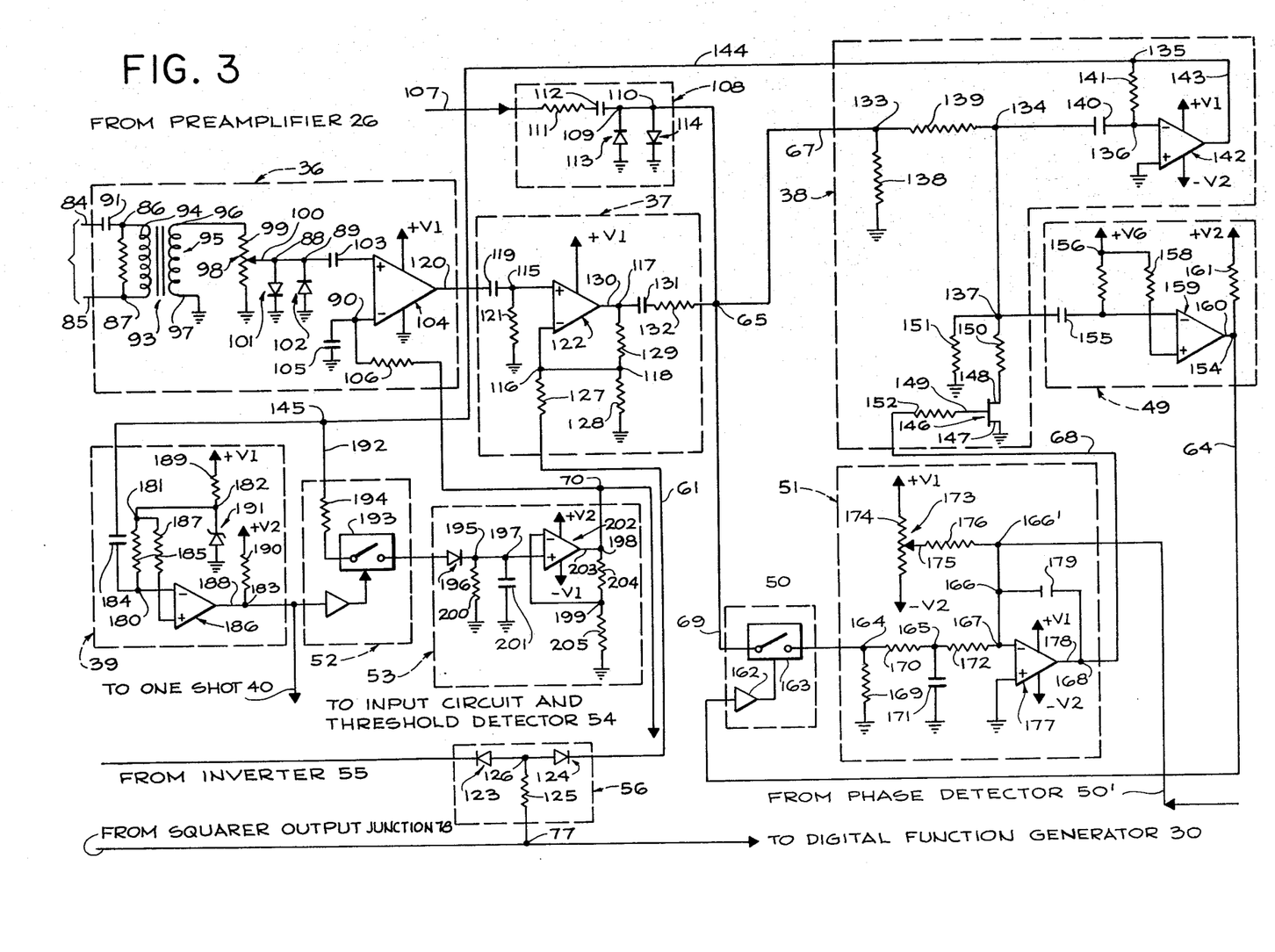
FIG. 3 is a schematic diagram of an input circuit, an AGC amplifier, a tracking filter, two zero crossing detectors, two phase detectors, two low pass filters and a clamp shown in FIG. 2.

In FIG. 3, input circuit 36 is shown for connection from preamplifier 26 in FIG. 1. Input circuit 36 has input leads 84 and 85. Input circuit 36 has various junctions 86, 87, 88, 89 and 90. A capacitor 91 is connected from input lead 84 to junction 86. Input lead 85 is connected to junction 87. A resistor 92 is connected between junctions 86 and 87. A transformer 93 is provided with a primary winding 94 and a secondary winding 95. Primary winding 94 is connected between junctions 86 and 87. Secondary winding 95 has leads 96 and 97, lead 97 being grounded. A potentiometer 98 is provided having a winding 99 and a wiper 100. Winding 99 is connected from transformer secondary lead 96 to ground. Wiper 100 is connected to junction 88. A diode 101 is connected from junction 88 to ground and poled to be conductive in a direction toward ground. A diode 102 is connected from junction 89 to ground and poled in a direction to be conductive toward junction 89. Junctions 88 and 89 are connected together.

A capacitor 103 is connected from junction 89 to the non-inverting input of a differential amplifier 104. Junction 90 is connected from the inverting input of amplifier 104. A capacitor 105 is connected from junction 90 to ground. A resistor 106 is connected from junction 70 to junction 90 (FIG. 2).

All of the blocks shown in FIG. 2 may be entirely conventional except the combination of dividers 400, 401 and 402 (not the dividers 400, 401 and 402 per se).

In FIG. 3, a calibration frequency may be provided over input lead 107, if desired, and impressed upon junction 65 through a circuit 108. Circuit 108 includes junctions 109 and 110. A resistor 111 and a capacitor 112 are connected in series in that order from lead 107 to junction 109. A diode 113 is connected from ground to junction 109, and is poled to be conductive in a direction toward junction 109. A diode 114 is connected from junction 110 to ground and is poled to be conductive in a direction toward ground. Junctions 109 and 110 are connected together. Junctions 110 and 65 are also connected together.

AGC amplifier 37 has junctions 115, 116, 117 and 118. A capacitor 119 is connected from an output lead 120 of amplifier 104 in input circuit 36 to junction 115. A resistor 121 is connected from junction 115 to ground. Junction 115 is also connected to the non-inverting input of an amplifier 122.

Clamp 56 includes diodes 123 and 124, and a resistor 125. Diodes 123 and 124 are connected in succession in that order from lead 80 to lead 61.

A junction is shown at 126. The anodes of diodes 123 and 124 are connected to junction 126. The cathode of diode 123 is connected to lead 80. The cathode of diode 124 is connected to lead 61.

Junction 77 is connected from junction 78, as described previously.

In FIG. 3, in AGC amplifier 37, a resistor 129 is connected between junctions 117 and 118. Junctions 116 and 118 are connected together. A resistor 128 is connected from junction 118 to ground. A resistor 127 is connected from lead 61 to junction 116. Amplifier 122 has an output lead 130 connected to junction 117.

A capacitor 131 and a resistor 132 are connected in series in that order from junction 117 to junction 65.

Again, in FIG. 3, junctions are provided at 133, 134, 135, 136 and 137. Junction 133 is connected from lead 67. A resistor 138 is connected from junction 133 to ground. A resistor 139 is connected between 133 and 134. A capacitor 140 is connected between junctions 134 and 136. A resistor 141 is connected between junctions 135 and 136. A differential amplifier 142 is provided having an inverting input connected from junction 136, a grounded non-inverting input, and an output lead 143 connected to junction 135.

Tracking filter 38 is connected to zero crossing detector 39 and phase detector 52 via a lead 144 connected from junction 135 in tracking filter 38 to a junction 145. Zero crossing detector 39 and phase detector 52 are connected from junction 145. In FIG. 3, tracking filter 38 has a field effect transistor 146 including a source 147, a drain 148 and a gate 149. Source 147 is grounded. A resistor 150 is connected from drain 148 to junction 137. Junctions 134 and 137 are connected together. A resistor 151 is connected from junction 137 to ground. A resistor 152 is connected from gate 149 to lead 68.

Zero crossing detector 49 has junctions at 153 and 154. A capacitor 155 is connected from junction 137 to junction 153. A third junction 156 is also provided and maintained at potential +V2. A resistor 157 is connected between junctions 153 and 156. A resistor 158 is connected from junction 156 to the non-inverting input lead of a differential amplifier 159. Junction 153 is connected to the inverting input load of amplifier 159. Amplifier 159 has an output lead 160 connected to junction 154. A resistor 161 is connected from junction 154 to potential +V2.

Lead 64 connects junction 154 to the input of a conventional amplifier 162 in phase detector 50. Phase detector 50 also includes a conventional electronic or transistor switch 163 which is connected from and operated by amplifier 162. Switch 163 is connected by a lead 69 from junction 65 to low pass filter 51 at junction 164 therein. Low pass filter 51 has various other junctions 165, 166, 166', 167 and 168. A resistor 169 is connected from junction 164 to ground. A resistor 170 is connected between junctions 164 and 165. A capacitor 171 is connected from junction 165 to ground. A resistor 172 is connected between junctions 165 and 167. Junctions 166 and 167 are connected together. A potentiometer is provided at 173 having a winding 174 and a wiper 175. Winding 174 is connected between +V1 and −V1. A resistor 176 is connected from wiper 175 to junction 166'. Junctions 166 and 166' are connected together. Junction 166' is also connected from phase detector 50'. A differential amplifier 177 is provided having an output lead 178 connected to junction 168. A capacitor 179 is connected between junctions 166 and 168. Junction 167 is connected to the inverting input lead of amplifier 177. The non-inverting input lead of amplifier 177 is connected to ground. Lead 68 and resistor 152 are connected in series in that order from junction 168 to gate 149 of field effect transistor 146.

Zero crossing detector 39 includes four junctions 180, 181, 182 and 183. A capacitor 184 is connected from junction 145 to junction 180. A resistor 185 is connected between junctions 180 and 181. An amplifier is provided at 186. A resistor 187 is connected from junction 181 to the non-inverting input of amplifier 186. Junction 180 is connected to the inverting input of amplifier 186. Amplifier 186 has an output lead 188 connected to junction 183. Junctions 181 and 182 are connected together. A resistor 189 is connected from junction 182 to potential +V1. A resistor 190 is connected from junction 183 to potential +V2. A zener diode 191 is connected from junction 182 to ground and is poled to be back biased between potential +V1.

Phase detector 52 may be identical to phase detector 50 and, therefore, will not be described except that phase detector 52 has an input lead 192 connected from junction 145 to a switch 193 via a resistor 194. Switch 193 is connected to low pass filter 53 to a junction 195 via a diode 196 poled to be conductive toward junction 195. Low pass filter 53 also has junctions 197, 198 and 199. A resistor 200 is connected from junction 195 to ground. A capacitor 201 is connected from junction 197 to ground. Junctions 195 and 197 are connected together. A differential amplifier 202 has an output lead 203 connected to junction 198. Junction 197 is connected to the non-inverting input of amplifier 202. The inverting input of amplifier 202 is connected from junction 199. Junctions 198 and 70 are connected together. A resistor 204 is connected between junctions 198 and 199. A resistor 205 is connected from junction 199 to ground.

Although phase detector 50' shown in FIG. 2 may be any conventional phase detector, it may be also of the type illustrated in FIG. 4 where junctions are provided at 300, 301, 302, 303, 304, 305, 306, 307, 308, 309, 310, 311 and 312.

A resistor 313 is connected from input circuit 36 to junction 300. Differential amplifiers are provided at 314, 315, 316 and 317. The inverting input of amplifier 314 is connected from junction 300. The non-inverting inputs of all of the amplifiers 314, 315, 316 and 317 are connected to ground. A resistor 318 is connected between junctions 300 and 301. A capacitor 319 is connected between junctions 301 and 302. Amplifiers 314, 315, 316 and 317 have respective output leads 320, 321, 322 and 323 connected respectively to junctions 301, 304, 310 and 312. A resistor 324 is connected from junction 303 to ground. The inverting input leads of amplifiers 315, 316 and 317 are connected respectively from junctions 303, 309 and 311. A resistor 325 is connected from junction 304 to a positive potential. A resistor 326 is connected from junction 305 to ground. A resistor 327 is connected between junctions 304 and 305. A field effect transistor (FET) is provided at 328. FET 328 is provided with a source 329 and a drain 330 connected from junctions 306 and 305, respectively. A capacitor 331 is connected from junction 306 to ground. A resistor 332 is connected between junctions 306 and 307. A capacitor 333 is connected between junctions 307 and ground. A resistor 334 is connected between junctions 307 and 309. Junctions 308 and 309 are connected together. A potentiometer is provided at 335 including a winding 336, and a wiper 337. A resistor 338 is connected from wiper 337 to junction 308. A single-pole, double-throw switch is provided at 339 including a pole 340, a contact 341 and another contact 342. Contact 341 is connected from junction 309. A resistor 343 is connected from contact 342 to low pass filter 51. Pole 340 is connected from junction 310. A capacitor 344 is connected between junctions 308 and 310.

FET 328 also has a gate 345 connected from junction 312 via a resistor 346. Phase detector 50' shown in FIG. 4 has an additional input lead 347. A capacitor 348 and a resistor 349 are connected in series in that order from input lead 347 to junction 311. A resistor 350 is provided and is connected from junction 311 to ground. A resistor 351 is connected from junction 312 to a positive potential.

Another potentiometer 352 is provided including a winding 353 and a wiper 354. A resistor 355 is connected from wiper 354 to junction 302.

The position of wiper 354 can be adjusted so as to adjust the average value of the waveform which appears at junction 302. The position of wiper 337 is adjusted to adjust the fixed phase shift, if any, between the signals received by phase detector 50' in FIG. 4 from input circuit 36 and driver amplifier 48. Circuit 36 and amplifier 48 are shown in FIG. 2.

Figure 5:
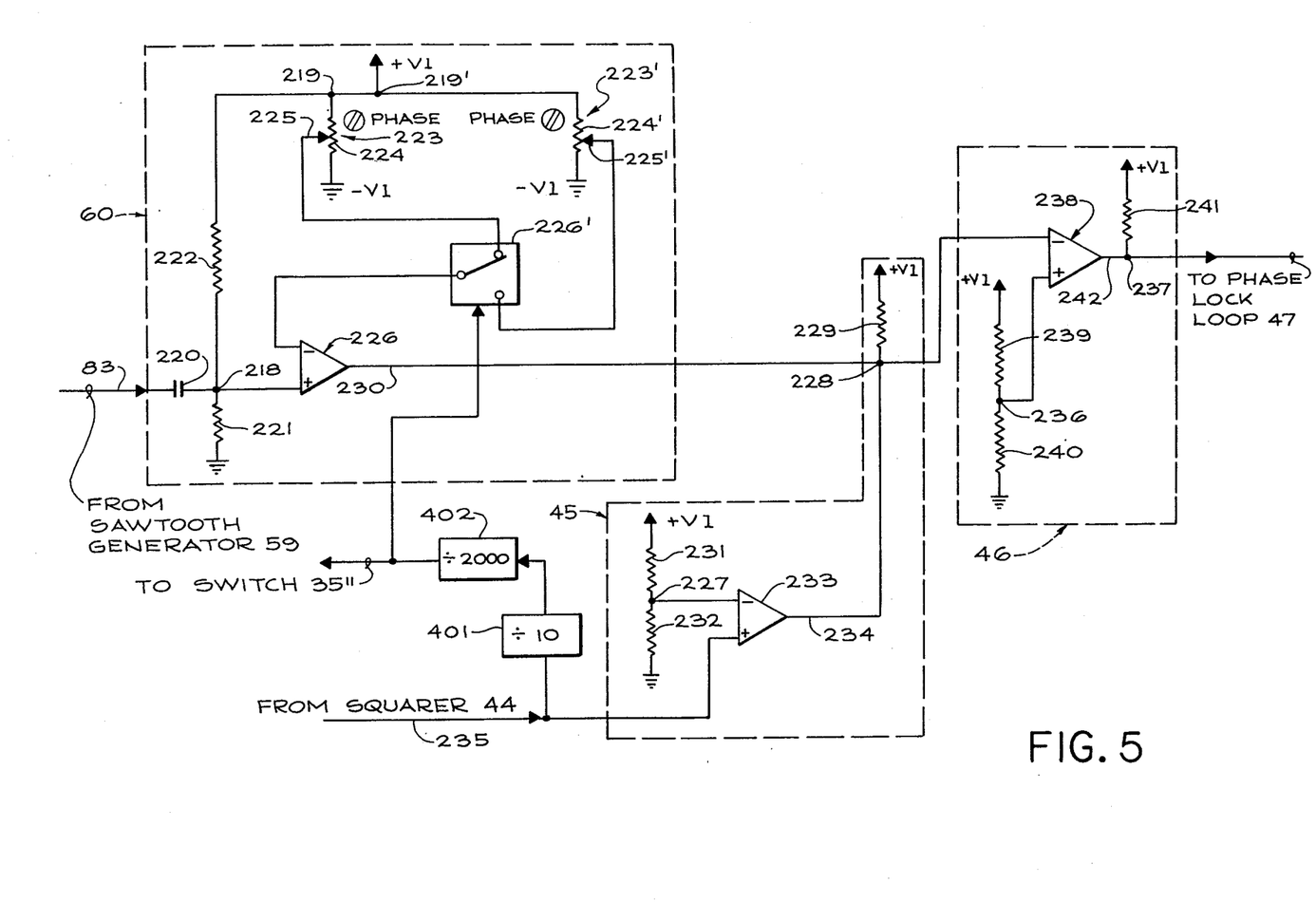
FIG. 5 is schematic diagrams of three blocks shown in FIG. 2.

In FIG. 5, phase adjustment circuit 60 is shown connected from sawtooth generator 59 over lead 83. Phase adjustment circuit 60 has three juntions 218, 219 and 219'. A capacitor 220 is connected from lead 83 to junction 218. A resistor 221 is connected from junction 218 to ground. A resistor 222 is connected between junctions 218 and 219. Junctions 219 and 219' are connected together. Junction 219 is maintained at potential +V1. A potentiometer 223 is shown having a winding 224 and a wiper 225. A potentiometer 223' has a winding 224' and a wiper 225'. Windings 224 and 224' are connected between junction 219' and ground. Wipers 225 and 225' are connected to the inverting input of differential amplifier 226 via switch 226'. The non-inverting input of amplifier 226 is connected from junction 218.

In FIG. 5, AND gate 45 has junctions 227 and 228. A resistor 229 is connected from potential +V1 to junction 228. In phase adjustment circuit 60, amplifier 226 has an output lead 230 connected to junction 228.

In AND gate 45, a resistor 231 is connected from junction 227 to potential +V1. A resistor 232 is connected from junction 227 to ground. AND gate 45 has a differential amplifier 233 with an output lead 234 connected to junction 228. Amplifier 233 has an inverting input connected from junction 227, and a non-inverting input connected from squarer 44 over a lead 235.

Inverter 46 has junctions 236 and 237. Inverter 46 also includes a differential amplifier 238 having an inverting input lead connected from AND gate junction 228 and a non-inverting input lead connected from junction 236. A resistor 239 is connected from junction 236 to potential +V1. A resistor 240 is connected from junction 236 to ground. A resistor 241 is connected from junction 237 to potential +V1. Amplifier 238 has an output lead 242 connected to junction 237. Junction 237 is connected to the input of phase lock loop 47.

In FIG. 1, the output lead 33' of loop circiut 29 is connected from the output of divider 402 in FIG. 2. Although the time is not important, utilization means 31 may remain unchanged and indicate density for a period of 10 seconds while utilization means 31' is updated each second for 10 seconds. In this case, switch 35" is maintained in the position not shown. Conversely, when utilization means 31' indicates viscosity and is unchanged for 10 seconds, utilization means 31 indicates density, and is updated each second for 10 seconds.

As can be seen in FIG. 1, the signal of the frequency of the electromechanical oscillator is impressed upon digital function generators 30 and 30' via output lead 34 of loop circuit 29. Digital function generator 30 receives these pulses via switch 35" and input lead thereto as indicated at 35.

Divider 400 in FIG. 2 makes the period of sawtooth generator 59 sufficiently long so that phase adjustment circuit 60 may pick off, alternately in synchronism with switch 35" shown in FIG. 1, phase relationships of +40° and −40° (the output of driver amplifier 48 in FIG. 2 relative to the output of preamplifier 26 shown in FIG. 1.

The combination of dividers 401 and 402 in FIG. 2 makes the period of switch 35" in FIG. 1 20 seconds.

In FIG. 5, when switch 226' is in the position shown, potentiometer wiper 225 is set to cause the output of amplifier 226 to lag the output of input circuit 36 by 40°. When switch 226' is in the position not shown, the position of wiper 225' on winding 224' of potentiometer 223' causes the output of amplifier 226 to lead the output of input circuit 36 by 40°.

Figure 6:
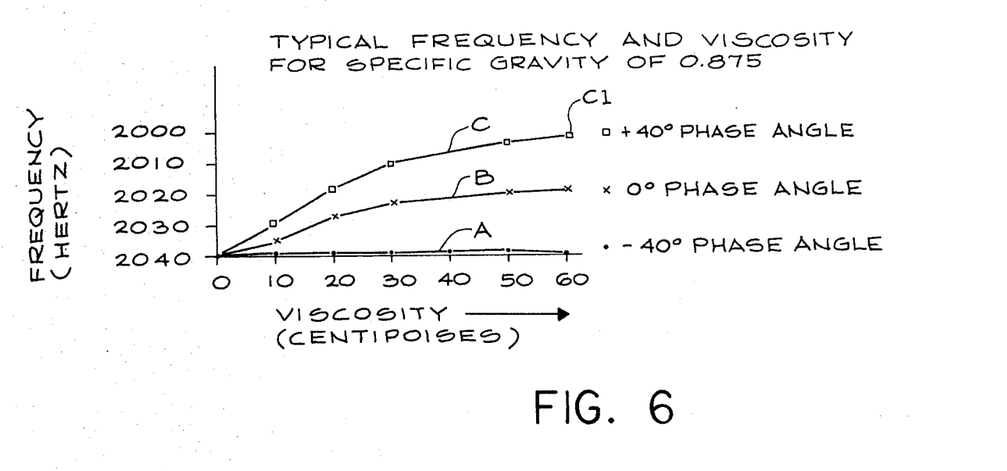
FIG. 6 is graphs of viscosity versus vibrational frequency.

In FIG. 6, curves A, B and C are shown. For a particular phase between the signals on leads 27 and 28 in FIG. 1, curves A, B and C are typical. Note that curve A is substantially insensitive to viscosity. The phase selected for curve A thus may indicate density accurately.

On the other hand, curve C is especially desirable to indicate viscosity. This is true because the point C1 has a corresponding frequency of, for example, 2,000, the range of which is about 40 hertz. On the other hand, for the curve A, the maximum frequency range for density of, say, 0 to 4 or 0 to 7 pounds per cubic foot might be 2.0 hertz. This is also true for curve C. The frequency change due to density change thus has no substantial effect on the accuracy of the curve C to indicate viscosity.

Figure 7:
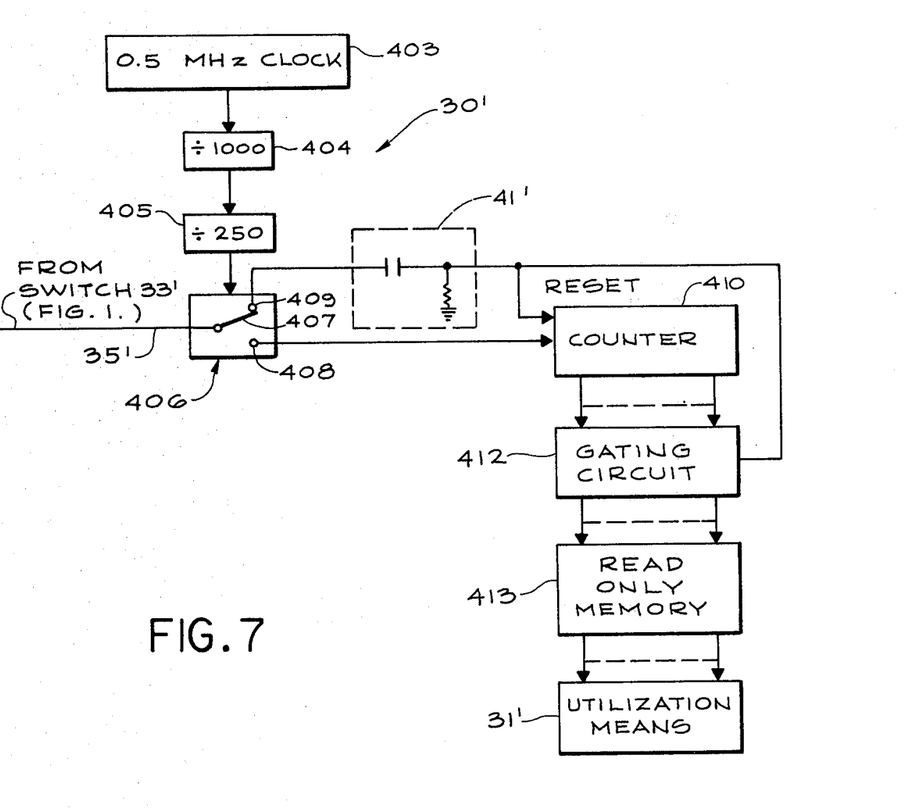
FIG. 7 is a schematic diagram of a viscosity function generator.

Digital function generator 30' is shown in FIGS. 1 and 7. Digital function generator 30' may be entirely conventional. An 0.5 megahertz clock is provided at 403 which is divided down by 1,000 by a divider 404, and is divided further by a divider 405.

Input lead 35' is connected from switch 35" shown in FIG. 1, as explained previously. A switch 406 is provided which is operated by the output of divider 405 and has a pole 407 that alternately engages contacts 408 and 409. Both of these contacts are connected to a counter 410, contact 409 being connected thereto through a differentiator 411. The output of differentiator 411 resets counter 410 and operates a gating circuit 412. A read only memory 413 and utilization means 31' are connected in succession in that order from gating circuit 412.

Each component part shown in FIG. 7 may be conventional. For example, see the said U.S. Pat. No. 3,878,374.

As will be evident from FIG. 7, the contents of counter 410 will be directly proportional to the magnitude of the frequency of the signal on input lead 35'. Read only memory 413 has an input register, not shown, into which the contents of counter 410 are shifted periodically be gating circuit 412 operated from switch 406 via differentiator 411. Read only memory 413 is then operated not by push button, but by the input thereto through the input storage register thereof. However, in all other respects, it operates in the manner of a conventional integrated circuit desk calculator.

For example, if a desk calculator read only memory carries the function $e^x$ where $e = 2.718281828$, the output of the memory will be that function when the input to the memory is some predetermined value of $x$. In a desk calculator, this predetermined value of $x$ is provided to the calculator by push buttons. In FIG. 7, read only memory 413 is provided with an input by the input register set by the gating circuit 412 which, in turn, is set by counter 410.

Read only memory 413 shown in FIG. 7 is constructed so as to provide the curve C shown in FIG. 6 but is otherwise conventional.

What is claimed is:

1. A fluid sensing instrument, said instrument comprising: a probe having an input lead, an output lead and a structure immersible in a fluid and vibratable responsive to a signal on said input lead; a loop circuit connected between said probe input and output leads to vibrate said structure; and means connected from said loop circuit to produce a signal which is a function of the viscosity of the fluid in which said structure is immersed, said means including a circuit to maintain said signal substantially more leading than $-40°$ relative to the vibration of said structure.

2. A fluid sensing instrument, said instrument comprising: a probe having an input lead, an output lead and a structure immersible in a fluid and vibratable responsive to a signal on said input lead; a loop circuit connected between said probe input and output leads to vibrate said structure; and means to shift the phase of said signal alternately to make the frequency of vibration of said structure insensitive to density and to viscosity, respectively.

3. The invention as defined in claim 2, wherein said signal is shifted in phase about $\pm 40°$ or more.

4. The invention as defined in claim 3, including a single-pole, double-throw switch and density and viscosity function generators operable synchronously with said means are connected from said loop circuit to produce outputs directly proportional to density and viscosity, respectively.

5. The invention as defined in claim 4, including an indicator connected from said density and viscosity function generators to indicate the density and viscosity of said fluid, respectively.

6. The invention as defined in claim 2, including a single-pole, double-throw switch and density and viscosity function generators operable synchronously with said means are connected from said loop circuit to produce outputs directly proportional to density and visc;sity, respectively.

7. The invention as defined in claim 6, including an indicator connected from said density and viscosity function generators to indicate the density and viscosity of said fluid, respectively.

* * * * *